United States Patent [19]
Kao et al.

[11] 4,111,948
[45] Sep. 5, 1978

[54] PROCESS FOR THE PREPARATION OF 4-METHYLTHIAZOLE

[75] Inventors: Henry S. Kao, Mountainside; William A. Sklarz, Edison; Leonard M. Weinstock, Belle Mead, all of N.J.

[73] Assignee: Merck & Co., Inc., Rahway, N.J.

[21] Appl. No.: 745,517

[22] Filed: Nov. 26, 1976

Related U.S. Application Data

[63] Continuation of Ser. No. 590,893, Jun. 27, 1975, abandoned, which is a continuation of Ser. No. 383,925, Jul. 30, 1973, abandoned.

[51] Int. Cl.$^2$ ............................................. C07D 277/02
[52] U.S. Cl. ............................ 260/302 R; 260/304 D
[58] Field of Search ..................................... 260/302 R

[56] References Cited

U.S. PATENT DOCUMENTS

| 2,179,984 | 11/1939 | Spiegelberg et al. | 260/302 R |
| 2,509,454 | 5/1950 | Russell | 260/302 R |

OTHER PUBLICATIONS

Elderfield (ed.), Heterocyclic Compounds, vol. 5, John Wiley & Sons, N.Y., 1957, p. 564.
Hackh's Chemical Dictionary, 3d. Edition, The Blakiston Company, Phila., 1944, p. 402.
Reid, Organic Chemistry of Bivalent Sulfur, vol. I., Chemical Publishing Co., N.Y., 1958, pp. 118–120.

*Primary Examiner*—Nicholas S. Rizzo
*Attorney, Agent, or Firm*—David L. Rose; Harry E. Westlake, Jr.

[57] ABSTRACT

Process for desulfurization of thiazoles including the removal of the mercapto group from 2-mercaptothiazoles and 2-mercaptobenzothiazoles and their derivatives by the oxidation with oxygen in the presence of an oxidation catalyst.

5 Claims, No Drawings

PROCESS FOR THE PREPARATION OF 4-METHYLTHIAZOLE

This is a continuation, of application Ser. No. 590,893 filed June 27, 1975, now abandoned, which is in turn a continuation of 383,925 filed July 30, 1973, now abandoned.

DISCLOSURE OF THE INVENTION

This invention relates to a new and useful process for the desulfurization of 2-mercaptothiazoles, and 2-mercaptobenzothiazoles. More particularly, this invention relates to the oxidative desulfurization of 2-mercaptothiazoles and 2-mercaptobenzothiazoles wherein the oxidation is carried out with oxygen in a liquid phase reaction medium in the presence of an oxidation catalyst.

Processes for desulfurization of organic molecules are, of course, known in the art. These processes are mostly reductive in character and involve employing catalysts designed for hydrodesulfurization. In the main, they are utilized in the petroleum industry. For example, feedstocks of aliphatic hydrocarbons having a high sulfur content are routinely subjected to treatment with hydrogen in the presence of reductive catalyst such as cobalt molybdate on an aluminum support to accomplish the desulfurization.

As a result, those molecules in the petroleum feedstock which contain sulfur as mercapto groups are reduced into the corresponding hydrodesulfurized product. Unfortunately, such catalytic hydrodesulfurization often results in the degradation of the heterocyclic molecules by removal of sulfur and/or nitrogen atoms.

The petroleum industry also employs oxidative techniques for sulfur removal, which results in the formation of sulfonic acid by-products. The catalysts employed in the present invention are however, not disclosed in the petroleum art. The nature of the oxidation of reduction by-products is immaterial in the petroleum industry, since removal of sulfur is their main concern. Any accompanying degradation is of little importance, so long as caloric value of the petroleum is not adversely affected.

Quite separate from any problem of degradation that may be associated with such reductive catalytic techniques, there is an economic expense associated with such process involving the use of equipment that can withstand high temperatures and pressures as well as the corrosive attack of the sulfur residues.

In addition, removal of mercapto groups from heterocyclic molecules by reductive techniques employing metal acids is known. Mercapto groups, for example, can be removed from position of a loweralkylthiazole by the use of iron and sulfuric acid. Such techniques have found commercial application, but unfortunately produce noxious and ecologically undesirable by-products which are $H_2S$ and an iron sludge rich in ferrous sulfide and ferrous sulfite. Each of these products presents disposal problems and costs which cannot be recovered from the value of the by-products and hence increase the total cost of the process both in economic and ecological terms.

In order to overcome these difficulties, we have now developed a new oxidative process for the desulfurization of 2-mercaptothiazoles and 2-mercaptobenzothiazoles, optionally further substituted at other positions of the thiazole ring, which is ecologically sound, economical, selective to mercapto groups, produces the sought after product in high yield, and further can be utilized in conventional processing equipment. In addition, degradation of the thiazole ring is substantially absent.

Therefore, the primary object of this invention is to provide for the selective desulfurization of substituted and unsubstituted 2-mercaptothiazole and 2-mercaptobenzothiazoles by oxidation to sulfinic acids or salts.

It is another object of this invention to provide for the oxidative desulfurization of such 2-mercaptothiazoles and 2-mercaptobenzothiazoles without any significant degradation or destruction of the thiazole ring.

A still further object of this invention is to provide an oxidative process for the removal of a mercapto group from the 2-position of a 2-mercaptothiazole and 2-mercaptobenzothiazole, to produce the corresponding 2-desmercaptothiazole and 2-desmercaptobenzothiazole in high yield. Additional objects and advantages will become apparent from a further reading of the following description.

The process of our invention can be summarized as residing in the concept of a process of desulfurizing 2-mercapto compounds with a gas phase oxygen containing oxidant in an alkaline liquid reaction medium.

The reaction medium has dispersed within itself a catalytic amount of a catalyst such as hemin, cyanocobalanine, finely divided activated carbon, metal phthalocyanines, especially phthalocyanines when the metal is vanadium, chromium, manganese, iron, cobalt, nickel and copper. Where an aqueous reaction medium is employed, it is desirable, in order to increase the solubility of the catalysts, especially the metal phthalocyanines, that a water-soluble salt derivative be used. In the case of the metal phthalocyanines, the alkali disulfonate salts of metal phthalocyanines are well adapted for use in aqueous medium.

The oxidation step is carried out by introducing gaseous oxygen in the form of air, pure oxygen, or oxygen in combination with other gases that are inert to reaction with reactants or products, such as nitrogen, helium, argon and the like into the reaction medium. After oxidation is complete, the mercapto group on the 2-mercaptothiazole has been oxidized to sulfinic acid, most usually as a sulfinate salt, the cation of which salt depends on the identity and nature of the alkaline source. If sodium hydroxide is the source of the alkaline pH, then the salt, of course, is sodium thiazole 2-sulfinate.

The sulfinate salt is then hydrolyzed either by the addition of acid to the reaction medium or heating an aqueous reaction medium to a temperature of 40°–110° C. The rate of desulfurization depends on the pH of the solution. At alkaline pH heating is required. At acidic pH, reaction takes place at lower temperatures. For example, at PH 11, heating at 100° C. for about 10 minutes is sufficient to effect the reaction; at pH 2, reaction is over in 2–3 minutes at room temperature.

The hydrolysis by-product is sulfur dioxide, which depending on pH either evolves as a gas or forms a salt, e.g., sodium bisulfite, and a thiazole. The desired thiazole product, can then be removed from the reaction medium by standard well known and accepted means for isolating and purifying reaction products. It is preferred, however, that the thiazole be removed either by azeotropic distillation or by extraction with a solvent which is not miscible with water, but rather forms a single phase with product. Benzene is an example of a satisfactory solvent. This solvent extraction may be followed by distillation to obtain a product of extraordinary purity.

The 2-mercaptothiazoles that are especially suited for desulfurization by the herein described process include those of the structure:

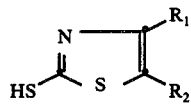

FORMULA I wherein $R_1$ and $R_2$ are independently $C_1$ to $C_4$ alkyl; aryl such as phenyl, naphthyl; hydrogen and hydroxy substituted $C_1$ to $C_4$ alkyl such as 2-hydroxyethyl, 2- and 3-hydroxypropyl, 3-hydroxybutyl, and the like;

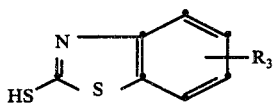

FORMULA II wherein $R_3$ is hydrogen, phenyl or halogen, e.g., chloro, bromo, or iodo, nitro, alkyl, lower alkylhydroxy, lower alkoxy and carboxylic.

Some preferred 2-mercaptothiazoles that undergo the process of this invention are those where $R_1$ is methyl and $R_2$ is hydrogen or 2-hydroxyethyl, of Formula I, as well as fused phenyl ring thiazoles of Formula II, especially those such as

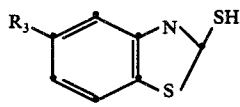

FORMULA III shown in Formula III, particularly where $R_3$ is chloro.

Generally, the process of our invention is carried out in an aqueous reaction medium employing sufficient water to dissolve the salt of 2-mercaptothiazole. Preferably, about 1.5 liters of water per mole of 2-mercaptothiazole is employed. When an aqueous reaction medium is used, an alkali hydroxide is the preferred base, sodium hydroxide being most preferred.

Other bases including the organic amines of from 1-12 carbon atoms including the cyclic amines, alkyl amines, heterocyclic amines, and alkanol amines such as pyridine, triethylamine, triethanolamine, aniline and the like can be used to advantage. Amines are especially useful bases when non-aqueous reaction mediums are employed. In such cases the amine itself can be used as the sole solvent or there can additionally be used alcohols such as amyl alcohol, isobutyl alcohol, as well as dimethylformamide, acetone, and acetonitrile. When these latter liquids are employed as solvents in the reaction medium, generally a lesser quantity of solvent is required than is the case when water alone is employed as solvent. Mixtures and solutions of the organic solvents and water can also be used, if desired.

The quantity of base employed effects the yield in that a quantity less than the stoichiometric amount, will diminish yield due to incomplete conversion. So it is preferable to use at least a stoichiometric amount of base and most preferably an excess. The amount of excess base depends on the catalyst employed. With cobalt phthalocynine disulfonic acid catalyst, for example, the optional range is between 1 to 1.2 moles and with activated charcoal, the optimal range is between 2 to 2.5 moles for each mole of 2-mercaptothiazole.

In carrying out the process, a reaction vessel is charged with the solvent, 2-mercaptothiazole, base, and catalyst. Air, gaseous oxygen, or gaseous oxygen in an inert gas is then introduced into the reaction medium.

The oxidation reaction can be carried out at pressures between from about 0.1 to about 100 atmospheres based on a partial pressure of oxygen of from about 0.1 to about 150 atmospheres when conducted at superatmospheric pressures, the reaction should be carried out with an inert gas contributing about at least 50% of the partial pressure. This precludes undesired oxidation side reactions and minimizes any explosion hazards.

The reaction is allowed to proceed preferably with agitation to intimately contact the phases present as well as to dissolve oxygen in the reaction medium.

Generally, the reaction can be carried out at ambient temperatures, e.g., 20° C., but a temperature range of 0° C. to 115° C. will provide satisfactory results. When the reaction is conducted at superatmospheric pressures, a temperature of 20° C. is usually adequate to effect oxidation. With less reactive 2-mercaptothiazoles, especially when operating at atmospheric pressures, a higher temperature is often indicated to effect reasonable rates.

The reaction is usually complete after 1 to 24 hours, and generally if conducted at higher pressures, is completed in a shorter time than if conducted at a lower pressure.

When the oxidation is complete, the reaction medium is optionally filtered to remove any solids present, and then hydrolyzed, either with acid or with heat, to the thiazole.

If the thiazole product is to be removed from the reaction medium by distillation, and a strong acid, e.g. one of a normality in excess of 0.5 and having a pH in aqueous solution of less than 3 has been introduced to perform the hydrolysis, it may be necessary to add a base such as alkali carbonate and the like to neutralize the reaction medium beforehand. Upon distillation, the distillate comprises a mixture of solvent and thiazole from which the thiazole can be removed by accepted and known techniques.

The following examples will further illustrate this invention.

EXAMPLE I

A mixture of 3.37 g. of 2-mercapto-4-methylthiazole (0.025 mole), 25 ml. of 2.24 N sodium hydroxide (0.056 mole) and 3.0 g. of activated charcoal (Nuchar C) 190 N is shaken under 30 pounds/in a gauge (psi) oxygen pressure for one hour. The mixture is filtered and the filtrate is made acidic (pH 3) with concentrated hydrochloric acid. After 10 minutes at 40° C. the solution is brought to pH 8 (NaOH) and distilled until the vapor temperature reaches 100° C. The distillate consists of a mixture of water and 4-methylthiazole (89% yield).

EXAMPE II

A mixture of 3.37 g. of 2-mercapto-4-methylthiazole (0.025 mole), 25 ml. of 1.084 N sodium hydroxide (0.027 mole) and 46 mg. of cobalt phthalocyanine disulfonate is shaken under 58 psi oxygen pressure for two hours. The mixture is worked up as described above. The yield of 4-methylthiazole is 81%.

What is claimed is:

1. A process for preparing 4-methylthiazole from 2-mercapto-4-methylthiazole comprising reacting 2-mercapto-4-methylthiazole in an aqueous alkali metal hydroxide solution with an oxidant consisting of oxygen or a mixture of oxygen and an inert gas at a pressure of from about 0.1 to about 100 atmospheres based on a partial pressure of oxygen of from about 0.1 to about 150 atmospheres, wherein there is dispersed in the aqueous solution cobalt phthalocyanine disulfonate to form a thiazole sulfinate salt and hydrolizing the thiazole sulfinate salt with acid or heating at a temperature of 40°–110° C.

2. A process according to claim 1 in which the oxidant is substantially pure oxygen.

3. A process according to claim 1 in which the temperature during the oxidation step is maintained between 0° C. and 115° C.

4. A process according to claim 1 wherein the separation of the thiazole from the reaction medium is carried out by distillation.

5. A process according to claim 1 wherein the separation step is carried out by extraction.

* * * * *